United States Patent [19]

Ueno

[11] Patent Number: 5,694,198
[45] Date of Patent: Dec. 2, 1997

[54] APPARATUS INCLUDING WAVEFORM RECTIFYING MEANS AND METHOD FOR EYE EXAMINATION

[75] Inventor: Yasunori Ueno, Kanagawa-ken, Japan

[73] Assignee: Nikon Corporation, Tokyo, Japan

[21] Appl. No.: 658,232

[22] Filed: Jun. 4, 1996

[30] Foreign Application Priority Data

Jun. 13, 1995 [JP] Japan ................................. 7-170412
Jun. 13, 1995 [JP] Japan ................................. 7-170413

[51] Int. Cl.$^6$ ................................. A61B 3/10; A61B 3/14
[52] U.S. Cl. ................................. 351/221; 351/208
[58] Field of Search ................................. 351/200, 205, 351/208, 221

[56] References Cited

U.S. PATENT DOCUMENTS

| | | | |
|---|---|---|---|
| 4,227,780 | 10/1980 | Ohta et al. | 351/208 |
| 4,390,255 | 6/1983 | Nohda et al. | 351/212 |
| 5,555,039 | 9/1996 | Iki et al. | 351/205 |

FOREIGN PATENT DOCUMENTS

| | | |
|---|---|---|
| A-55-86437 | 6/1980 | Japan . |
| 61-122837 | 6/1986 | Japan . |
| 62-41637 | 2/1987 | Japan . |

*Primary Examiner*—Huy Mai
*Attorney, Agent, or Firm*—Oliff & Berridge

[57] ABSTRACT

An eye examination apparatus enables the examination of a condition of an eye (e.g., the refractive power of an eye, the focus state of the apparatus on the eye) being examined with high precision even when there is a partial obstruction such as a partial crystalline lens cloudiness or partial vitreum cloudiness in the eyeball of the eye. A light projecting optical system projects light (an image) onto a fundus of the eye being examined. A light-receiving element receives the light (the image) reflected from the eye fundus and outputs a waveform representative of the received reflected light. A waveform rectifying device rectifies the output waveform from the light-receiving element by correcting a disorder of the light-receiving element output waveform caused by partial obstruction in the eyeball or the like when such a disorder is determined to be present. The condition (e.g., refractive power, the focus states, etc.) of the partially obstructed eye is then determined using the rectified waveform from the waveform rectifying device. The eye examining device can further include an illuminating optical system that emits illuminating light on the eye fundus and a photographic optical system for photographing or observing the eye fundus illuminated by the illuminating optical system.

33 Claims, 6 Drawing Sheets

APPARATUS INCLUDING WAVEFORM RECTIFYING MEANS AND METHOD FOR EYE EXAMINATION

BACKGROUND OF THE INVENTION

1. Field of the Invention

The present invention relates to eye examination apparatus that output a waveform based on the reflection of light from the eyeball of the eye being examined.

2. Description of Related Art

In general, with apparatus that observe and make measurements of eyes, it is extremely difficult to focus the apparatus (for example, a photographing optical system and/or an observing optical system of the apparatus) on the fundus of the eye because of poor contrast and a limited amount of light caused by the low reflectivity of the eye fundus. When observing the eye fundus image using fluorescent light, contrast becomes difficult to analyze because the eye fundus image is almost colorless. For example, the observation system becomes black and white, making focussing even more difficult due to the loss of contrast.

For example, with a conventional ophthalmologic apparatus, it is very difficult to focus during general photography and during fluorescent light photography. Focus state detection is performed by projecting a light image onto a fundus of the eye and then detecting the light that is reflected from the eye by using a light-receiving element. The focus state is detected by analyzing an output signal of the light-receiving element. However, when partial crystalline lens cloudiness or partial vitreum cloudiness is present in the eyeball of the eye being examined, the quality of the (reflected) eye fundus image decreases severely and a corresponding disorder is created in the output signal of the light-receiving element, to the extent that focus state detection is impossible at times.

Another type of eye examination apparatus is known as an objective eye refractive power measuring apparatus. One type of objective eye refractive power measuring apparatus performs refractive power detection when the eye being examined is fixed and relaxed. For example, in a conventional apparatus where the eye fundus being examined is scanned by light rays, the scanning light rays reflected from the eye fundus are received by a light-receiving element, as disclosed in Japanese Laid-Open Patent Publication No. 55-86437, which corresponds to U.S. Pat. No. 4,390,255, the disclosure of which is incorporated herein by reference. Measurement of the refractive power is accomplished based on an output signal of the light-receiving element. Again however, when partial crystalline lens cloudiness or partial vitreum cloudiness is present in the eyeball of the eye being examined, disorder is created in the output signal from the light-receiving element to the extent that measuring the refractive power becomes impossible or generates only low reliability measured values.

SUMMARY OF THE INVENTION

It is an object of the present invention to solve at least the above-described problems of conventional eye examination apparatus.

It is another object of the present invention to provide an eye examination apparatus and method for using same that precisely measures a condition in the eye being examined when there is partial crystalline lens cloudiness, partial vitreum cloudiness or the like in the eyeball.

It is another object of the present invention to provide an eye examination apparatus that can determine and display a degree of cloudiness in the eye based on an amount of waveform disorder in a waveform signal determined based on light reflected by the eye being examined.

In order to achieve the above and other objects, and to overcome the shortcomings in the prior art, eye examination apparatus according to embodiments of the present invention include a waveform rectifying device that rectifies a waveform signal output by a light-receiving element when the waveform signal includes a disorder caused by a partial obstruction in the eye. The waveform rectifying device eliminates the disorder from the waveform signal and outputs a rectified waveform signal. The eye examination apparatus also includes a light projecting optical system including a light source that projects light onto a fundus of an eye being examined, the light-receiving element that receives light reflected from the eye fundus and outputs the waveform signal representing an amount of the received reflected light, and an examining device that examines a condition of the eye based on the waveform signal. When the waveform rectifying device rectifies a waveform disorder, the eye examining device examines the condition of the eye based on the rectified waveform signal. The eye examination apparatus can further determine and display a degree of cloudiness in the eye based on an amount of waveform disorder in the waveform signal output by the light-receiving element.

According to one embodiment of the present invention, the eye examination apparatus is an eye refractive power measuring apparatus that precisely measures a refractive power of the eye being examined even when there is partial crystalline lens cloudiness, partial vitreum cloudiness or the like in the eyeball.

According to another embodiment of the present invention, the eye examination apparatus is an ophthalmologic apparatus that performs precise focus state detection with respect to the eye being examined even when there is partial crystalline lens cloudiness, partial vitreum cloudiness or the like in the eyeball.

Other objects, advantages and salient features of the invention will become apparent from the detailed description taken in conjunction with the annexed drawings, which illustrate preferred embodiments of the invention.

BRIEF DESCRIPTION OF THE DRAWINGS

The invention will be described with reference to the following drawings in which like reference numerals refer to like elements and wherein.

DETAILED DESCRIPTION OF PREFERRED EMBODIMENTS

Figure 1:
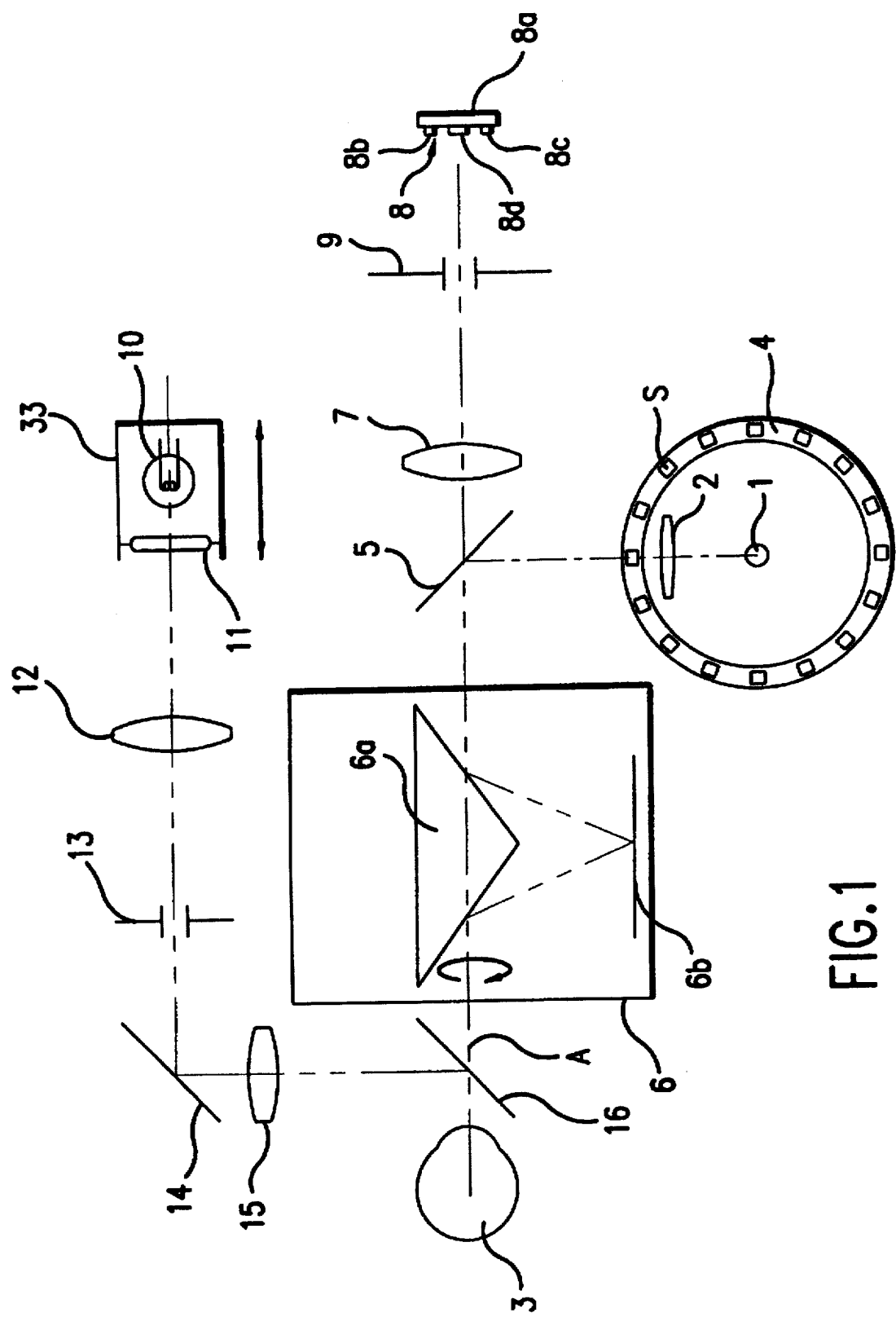
FIG. 1 is a schematic drawing of an optical system of an eye refractive power measuring apparatus according to an embodiment of the present invention.

An optical system in an eye refractive power measuring apparatus according to a first embodiment of the present invention is shown in FIG. 1. The eye refractive power measuring apparatus of the present embodiment is equipped with a refractive power detector and a fogging apparatus. The measuring principle of the refractive power detector is based on retinoscopy. As is well known to one of ordinary skill in the art, retinoscopy is a method that measures the eye refractive power by detecting the movement speed of shadows on the pupil. An objective eye refractive power detector using retinoscopy is disclosed in U.S. Pat. No. 4,390,255, the disclosure of which is incorporated herein by reference.

As shown in FIG. 1, the eye refractive power measuring apparatus includes a light-emitting diode 1 that emits infrared light and acts as a light source for refractive power measurement. An image of the infrared light emitted from the light-emitting diode 1 is formed by a condenser lens 2 on the pupil of an eye 3 being examined. The light-emitting diode 1 and the condenser lens 2 are surrounded by a chopper 4 that includes a hollow cylinder. A plurality of slit-shaped openings S are positioned around the circumference of the chopper 4. The long direction of each of the slit-shaped openings S is perpendicular to the plane of the paper in FIG. 1.

The chopper 4 is rotated about the light-emitting diode 1 by a driving system (not shown). The line-shaped light rays that pass through the slit-shaped openings S in the chopper 4 are incident on a half mirror 5. The half mirror 5 reflects the infrared light from the light-emitting diode 1 toward the eye 3 being examined.

The infrared light reflected by the half mirror 5 is incident on a measuring line rotating system 6 that includes a prism 6a and a mirror 6b. The measuring line rotating system 6 is an optical system used to observe the astigmatic state of the eye 3 being examined. The prism 6a and the mirror 6b integrally rotate about an optical axis A. Thus, the line direction of the line-shaped light rays incident on the eye 3 being examined form a light source image that continually changes on the pupil surface of the eye 3. Thus, a fundus of the eye 3 is scanned by the line-shaped light rays created by the rotation of the chopper 4.

Infrared light reflected from the eye 3 being examined passes through the measuring line rotating system 6 and the half mirror 5, and then is incident on an objective lens 7. The reflected image from the pupil surface of the eye 3 being examined passes through the objective lens 7 and is formed onto a light-receiving unit 8 through a diaphragm 9. The diaphragm 9 has a slit-shaped opening. The long direction of the slit-shaped opening in the diaphragm 9 is in the direction perpendicular to the plane of the paper in FIG. 1. The diaphragm 9 is substantially at the focal point of the objective lens 7.

Figure 2:
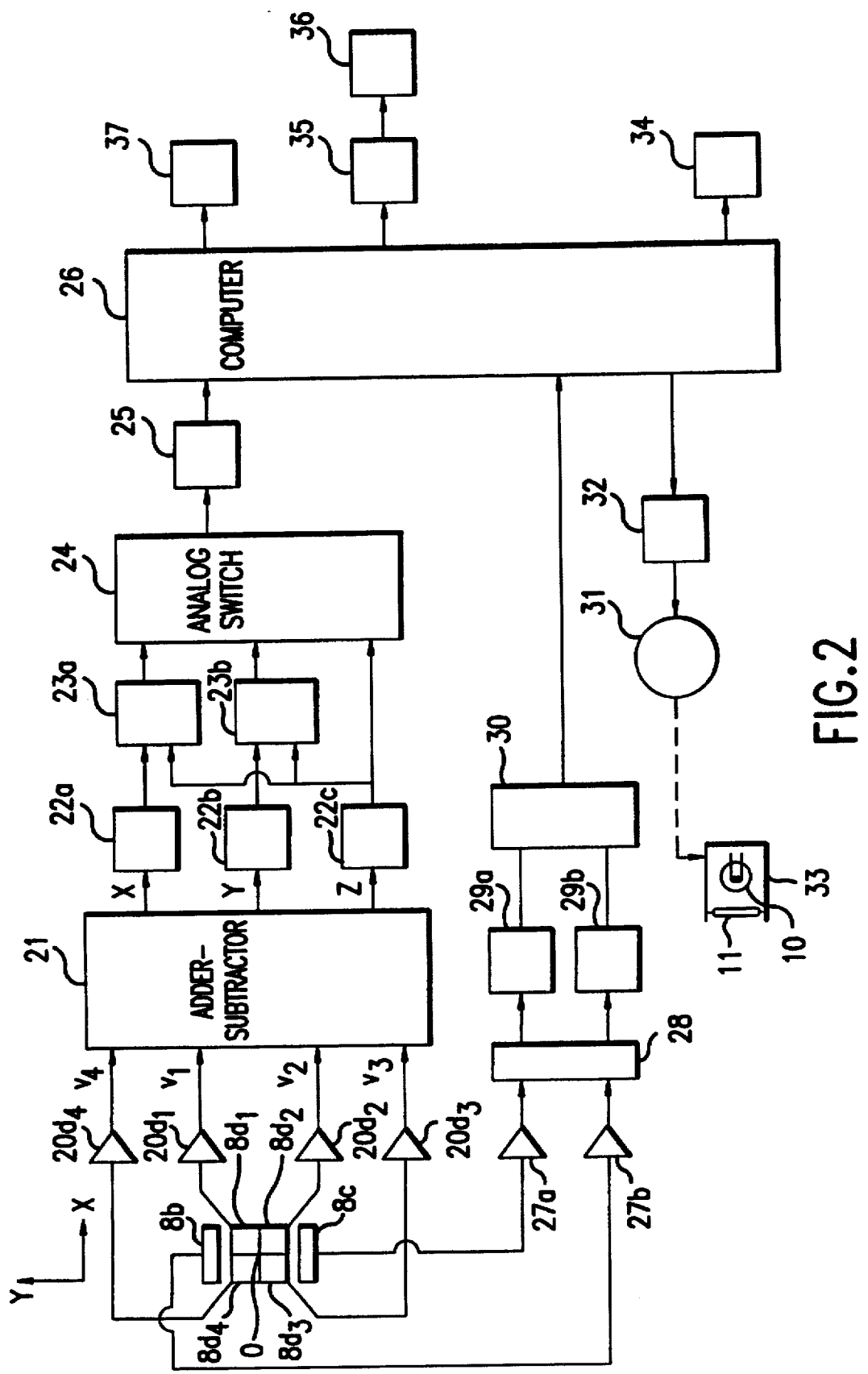
FIG. 2 is a block diagram of an electrical processing system of the FIG. 1 embodiment.

The light-receiving unit 8 includes a base plate 8a, photoelectric conversion elements 8b and 8c and a four partition photoelectric conversion element 8d. The photoelectric conversion elements 8b and 8c are used for refractive power measurement. The photoelectric conversion element 8d is used for position shifting detection. As shown in FIG. 1, the photoelectric conversion elements 8b and 8c are positioned in a direction corresponding to the scanning direction of the line-shaped light rays on the eye 3 being examined. The four partition photoelectric conversion element 8d is positioned between the photoelectric conversion elements 8b and 8c. Four photoelectric conversion elements $8d_1$–$8d_4$ of the four partition photoelectric conversion elements are arranged as shown in FIG. 2. FIG. 2 depicts the light-receiving unit 8 from the direction of the objective lens 7. A center point O of the four photoelectric conversion elements $8d_1$–$8d_4$ coincides with the optical axis A of the objective lens 7.

Thus, the optical system of the refractive power detector includes the light-emitting diode 1, the condenser lens 2, the chopper 4, the half mirror 5, the measuring line rotating system 6, the objective lens 7, the light-receiving unit 8 and the diaphragm 9.

An optical system of the fogging apparatus includes a target 11 and a visible light source 10 that emits visible light rays to illuminate the character 11. The target 11 and the visible light source 10 are integrally supported by a support member 33. The support member 33 is moved back and forth along the direction of an optical axis (the direction indicated by the arrows in FIG. 1) by a stepping motor 31 (see FIG. 2).

Light from the target 11, which has been illuminated by the visible light source 10, passes through a projection lens 12 and a diaphragm 13 and then is reflected by a mirror 14 to impinge on a lens 15. The light from the target 11 that passes through the lens 15 is reflected by a half mirror 16 in the direction of the eye 3 being examined and projects onto the retina via the crystalline lens of the eye 3. Thus, an image of the target 11 is formed on the retina of the eye 3 being examined. The lens 15 is used to position the diaphragm 13 optically conjugate with the pupil of the eye 3 being examined. In other words, through the function of the lens 15, the size of the pupil is kept optically constant even if the eye 3 being examined changes. Therefore, the depth of the field can be kept constant.

If the refractive state of the eye 3 being examined is in a constant state, the position of the target 11 is fixed at a specific point on the optical axis and a corresponding image of the target 11 is formed on the retina of the eye 3 being examined. In other words, there is a one-to-one relationship between the refractive powers of the eye 3 being examined and the position of the target 11 on the optical axis when an image of the target 11 is formed on the retina of the eye 3 being examined.

As detailed above, the optical system of the fogging apparatus includes the visible light source 10, the target 11, the support member 33, the projecting lens 12, the diaphragm 13, the mirror 14, the lens 15 and the half mirror 16.

An electrical processing system of the eye refractive power measuring apparatus is shown in FIG. 2. The signal processing sequence of the eye refractive power measuring apparatus will now be described.

The photoelectric current created in each of the four photoelectric conversion elements $8d_1$–$8d_4$ that receive light is converted into an electric voltage signal with low impedance in four corresponding amplifiers $20d_1$–$20d_4$. The voltage signals output from the amplifiers $20d_1$–$20d_4$ are input into an adder-subtractor 21. The adder-subtractor 21 outputs an X signal corresponding to a position shift in the X direction (the direction indicated by an X arrow in FIG. 2) of the light reflected from the cornea. The adder-subtractor 21 further outputs a Y signal corresponding to a position shift in the Y direction (the direction indicated by a Y arrow in FIG. 2) of the light reflected from the cornea and a sum signal Z indicating the intensity of the light reflected from the cornea. The X and the Y directions are in the plane perpendicular to the optical axis A as shown in FIG. 1.

If the outputs of the amplifiers $20d_1$–$20d_4$ are called $v_1$ through $v_4$, respectively, the X signal is $(v_1+v_2)-(v_3+v_4)$, and the Y signal is $(v_1+v_4)-(v_2+v_3)$. The three signals X, Y and Z output from the adder-subtractor 21 are converted into direct voltage with the chopping frequency component suppressed in low range filters 22a–22c, respectively. Analog dividers 23a and 23b normalize the X signal and Y signal, respectively, to prevent the coordinate signals from changing because of differences in the cornea reflectivity.

The normalized X coordinate signal, the normalized Y coordinate signal and the sum signal Z are alternately output to an analog switch 24. The signals output by the analog switch 24 are converted into digital signals in an A/D converter 25, and are then input to a computer 26. The computer 26 drives a display circuit 37 that can display the digitized X coordinate signal and the digitized Y coordinate signal.

The detection of the refractive power is performed by measuring the phase difference between the signals output from the two photoelectric conversion elements 8b and 8c. The eye fundus 3 is scanned by line-shaped light rays generated by the rotation of the chopper 4. Accordingly, when the eye 3 being examined is a normal eye, the position of the slit in the diaphragm 9 corresponds exactly to the neutral point. Consequently, the light rays emitted through the opening of the slit 9 become brighter and darker uniformly and the phases of the output signals of the two photoelectric conversion elements 8b and 8c are the same.

When the eye 3 being examined is not a normal eye, light and dark stripes corresponding to the respective states of refractive error in the eye 3 are emitted from the opening of the diaphragm 9. Accordingly, the phases of the output signals from the photoelectric conversion elements 8b and 8c differ with the states of refractive error in the eye 3 being examined. In this way, the refractive power of the eye 3 being examined can be determined from the phase difference between the output signals from the photoelectric conversion elements 8b and 8c.

Figure 3:
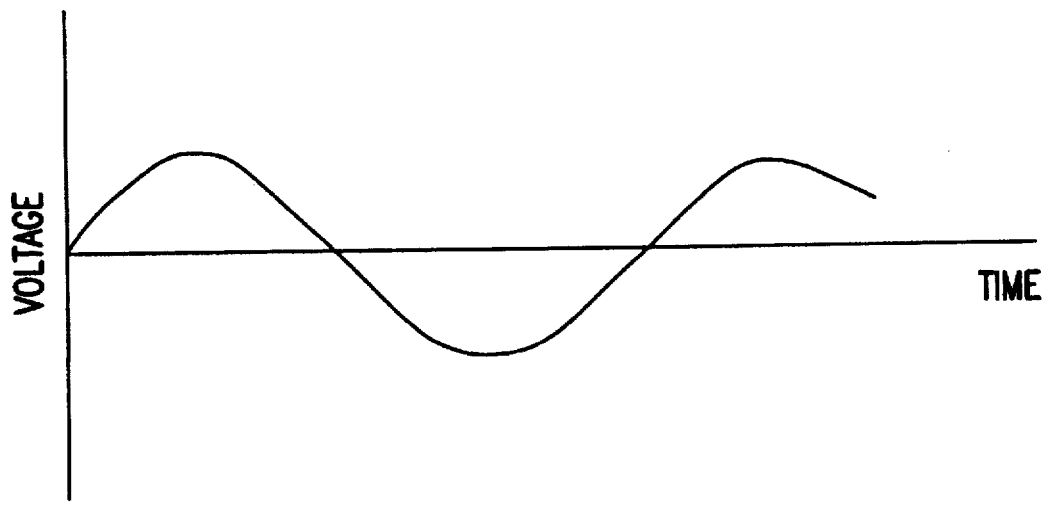
FIG. 3 shows the output waveform representing the refractive power for a normal (i.e., non-cloudy) eye output by the FIG. 1 embodiment.
Figure 4:
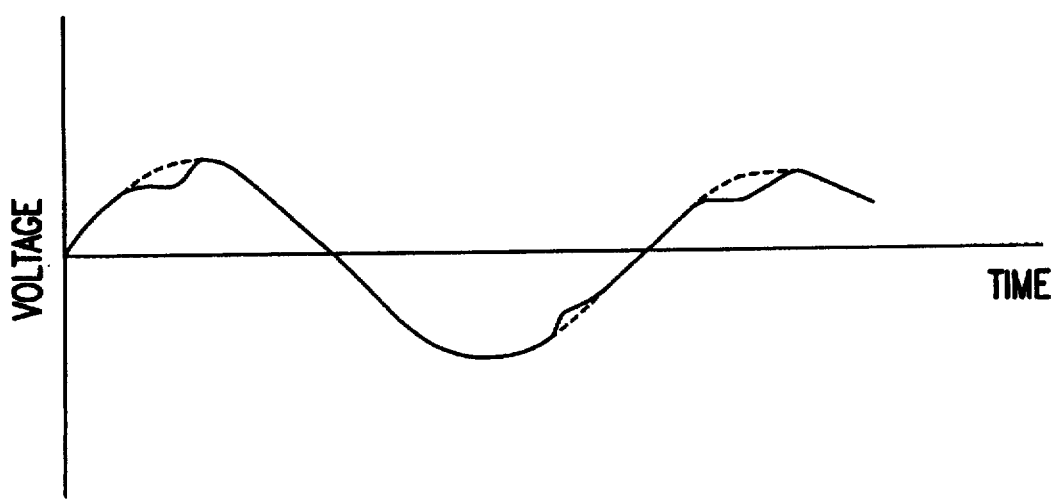
FIG. 4 shows the output waveform representing the refractive power for an eye having partial crystalline lens cloudiness or partial vitreum cloudiness output by the FIG. 1 embodiment and also shows corrections made to that waveform by the present invention.

An example of an output waveform from the photoelectric conversion elements 8b and 8c when the refractive power is measured for an eye having no cloudiness is shown in FIG. 3. An example of a refractive power output waveform from the photoelectric conversion elements 8b and 8c for an eye having partial crystalline lens cloudiness or partial vitreum cloudiness is shown in FIG. 4.

When the refractive power is measured for an eye having no partial cloudiness (FIG. 3), no waveform disorder is created in the output waveform from the photoelectric conversion elements 8b and 8c. Thus, the refractive power of the eye 3 being examined can be accurately determined from the phase difference between each of the two output waveforms from the photoelectric conversion elements 8b and 8c.

However, when there is crystalline lens cloudiness, vitreum cloudiness, or other obstruction in the eyeball of the eye 3 being examined, it is difficult to determine the refractive power of the eye being examined based on the output waveforms from the photoelectric conversion elements 8b and 8c. Naturally, when the eyeball of the eye 3 is uniformly cloudy, it is possible to measure with some degree of precision the refractive power of the eye 3 being examined by increasing the amount of incident light. However, when there is partial cloudiness in the eyeball of the eye 3 being examined, waveform disorder is created in the output waveforms, as shown in FIG. 4. As a result, it is very difficult to accurately measure the phase difference between each output waveform; and therefore, the refractive power of the eye 3 being examined using the output waveforms from the photoelectric conversion elements 8b and 8c.

To address this problem of partial cloudiness, etc., in the first preferred embodiment of the invention, the output waveforms from the photoelectric conversion elements 8b and 8c are stored in memory. Then, the output waveforms are analyzed to determine whether there are discontinuous parts or irregular parts in the output waveforms. Alternatively, the output waveforms can be directly analyzed. The analysis for disorders in the waveforms can be performed in various well known ways. When discontinuous parts or irregular parts are determined to exist in the waveforms, the discontinuous parts or irregular parts are then interpolated as indicated by the dashed line in FIG. 4. Various well known techniques for eliminating disorders such as discontinuities and irregularities in waveforms can be employed. In this way, the phase difference between each of the output waveforms, and hence the refractive power of the eye 3 being examined, can be accurately measured. In other words, the output waveforms are corrected by interpolating the disordered components of the output waveforms. The corrected waveforms can then be used to determine the phase difference.

As shown in FIG. 2, the outputs from the two photoelectric conversion elements 8b and 8c are input into a microcomputer 28 through buffers 27b and 27a, respectively. In the microcomputer 28, the output waveforms from the photoelectric conversion elements 8b and 8c can be stored in memory. Then, the output waveforms are analyzed (using well known techniques) to determine whether there are discontinuous parts or irregular parts in the output waveforms. When discontinuous parts or irregular parts are determined, the output waveforms are rectified by interpolating the discontinuous parts or irregular parts. Thus, the microcomputer 28 includes a waveform rectifying unit that rectifies the output waveforms by correcting the waveform disorder caused by partial cloudiness or the like in the eye 3 being examined.

The waveforms rectified by the microcomputer 28 are then shaped, for example, into square waves in waveform shaping circuits 29a and 29b. The outputs from the waveform shaping circuits 29b and 29a are converted using a phase difference counter 30 into pulse numbers corresponding to the phase difference between the shaped waveforms. The pulse numbers are input into the computer 26. The computer 26 alternately receives the signals from the A/D converter 25 and the phase difference counter 30.

When the X signal and the Y signal substantially indicate the zero level while the sum signal Z is above a predetermined level (i.e., an alignment signal), a predetermined pulse is output as a driving signal to a driving circuit 32 of the stepping motor 31 in accordance with the digital signal output from the phase difference counter 30. In other words, the alignment signal is used to initially align the eye 3 being examined within the eye refractive power measuring apparatus. Here, the sum signal Z is used because the X signal and the Y signal substantially indicate zero even when the positions of the eye 3 being examined and the eye refractive power measuring apparatus are shifted by a large amount.

The stepping motor 31 drives the support member 33 that integrally supports the visible light source 10 and the target 11. As described above, there is a one-to-one correspondence between the refractive powers of the eye 3 being examined and the positions of the target 11 and its corresponding image formed on the retina of the eye 3 being examined. To cause the eye 3 being examined to relax, the target image is formed slightly to the front of the retina so that the eye 3 being examined is directed to a distant point. Thus, the support member 33 position and the target 11 can be determined using the signal corresponding to the refractive power of the eye 3 being examined (the signal corresponding to the phase difference between the output signals from the photoelectric conversion elements 8b and 8c) modified slightly to relax the eye 3.

A sequence for operating the eye refractive power measuring apparatus will now be described. A user first verifies that there is no discrepancy in the positions of the eye 3 being examined and the eye refractive power measuring apparatus. The user then verifies that the eyelashes of the person being examined are not in the measuring light path. Next, the user turns a measuring start switch 34 ON to input a measurement start signal to the computer 26. When the measurement start signal is received, the computer 26 operates the automatic fogging apparatus. When the fluctuations in the output of the phase difference counter 30 become small because the feedback system reaches a stable state, the computer 26 receives the output signal from the phase difference counter 30. The computer 26 converts the phase difference counter 30 signal into a count, and inputs the count into a CRT controller 35 of a CRT monitor 36. In this way, the refractive power (represented by the count) of the eye 3 being examined, which is measured in a substantially relaxed state, is displayed on the CRT monitor 36.

Thus, in the first preferred embodiment, highly precise refractive power measurement is performed even when there is partial crystalline lens cloudiness or partial vitreum cloudiness in the eyeball of the eye 3 being examined. Further, the degree of cloudiness in the eyeball can be detected based on an amount of waveform disorder in the output waveforms. The detected degree of cloudiness can then be converted into a numerical value or the like in a well known manner, which is displayed on the CRT monitor 36 or the like.

In the first preferred embodiment, retinoscopy is used as the measurement principle of the eye refractive power detector. However, retinoscopy is but one of the measuring principles for eye refractive power detectors. Accordingly, the present invention is not limited to this measuring principle, for other measuring principles can also be applied.

An ophthalmologic apparatus according to a second preferred embodiment of the present invention is described with reference to FIGS. 5–12. The ophthalmologic apparatus includes an illuminating optical system that illuminates the fundus of an eye being examined, an index mark projecting optical system that projects an index mark onto the eye fundus being examined, a focus state detecting system that receives light from the index mark projected onto the eye fundus and performs focus state detection on the eye fundus, an observing optical system that enables an observer to observe the state of the eye fundus being examined and a photographic optical system that enables one to photograph the state of the eye fundus being examined.

Figure 5:
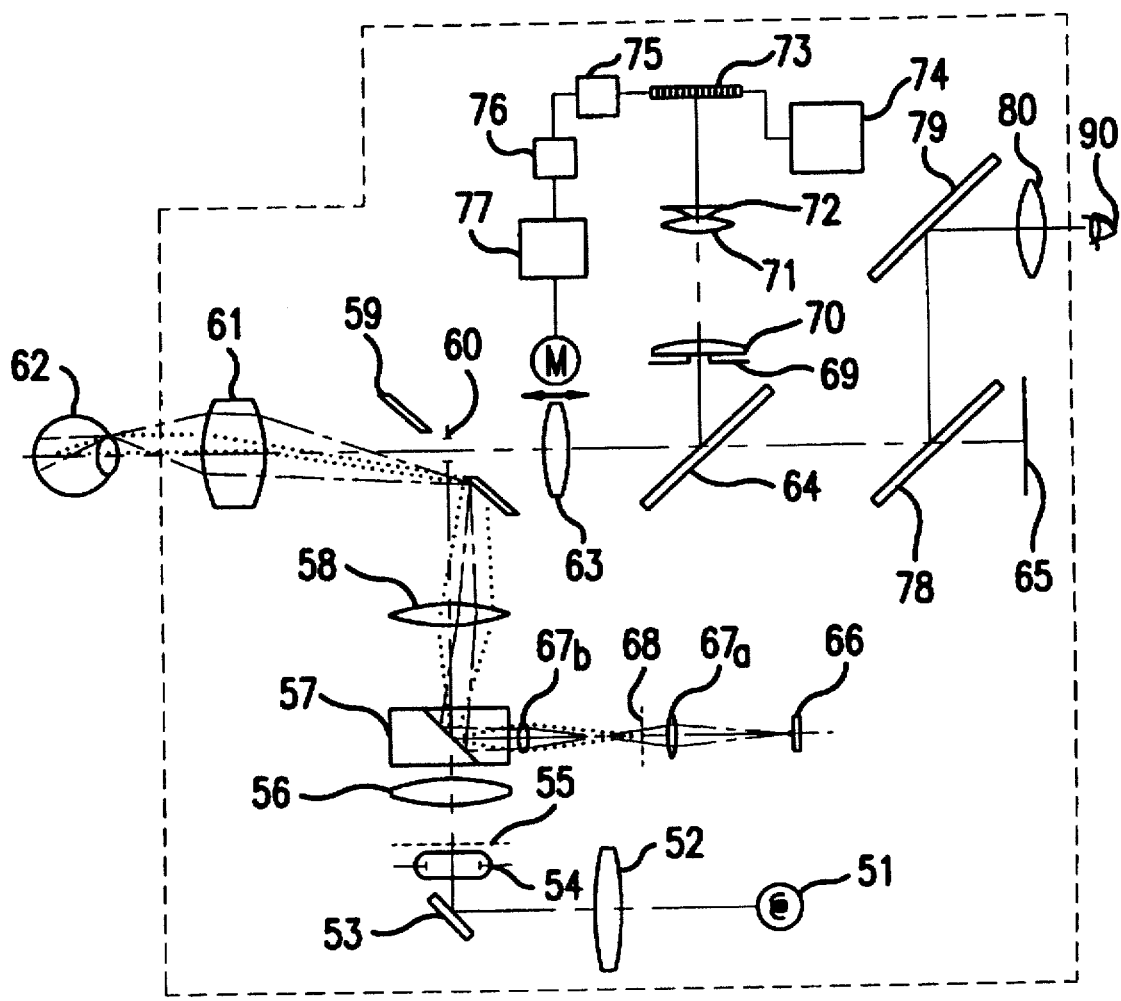
FIG. 5 is a schematic drawing showing an ophthalmologic apparatus according to another embodiment of the present invention.
Figure 7:
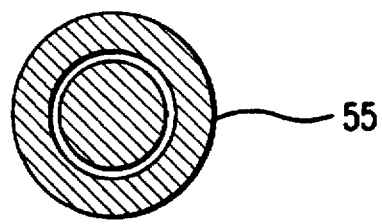
FIG. 7 is a view along the optical axis of a ring slit included in the FIG. 5 embodiment showing a circular opening in the ring slit.

The illuminating optical system includes an observation-use illuminating light source 51. The light emitted from the observation-use illuminating light source 51 is incident on a reflecting mirror 53 through a light source relay lens 52, and is reflected upward as shown in FIG. 5. The light reflected by the reflecting mirror 53 is incident on a ring slit relay lens 56 through a ring slit 55. The ring slit 55 is shown in FIG. 7 and has a circular slit opening centered about an optical axis. A strobe tube 54 is an illuminating light source for photography. The strobe tube 54 is located at a position conjugate with the observation-use illuminating light source 51 through the light source relay lens 52.

Light, which has passed through the ring slit relay lens 56 (light from the strobe tube 54 and light from the observation-use illuminating light source 51) passes through a dichroic prism 57 and is incident on a mirror 59 through another ring slit relay lens 58. The mirror 59 has a central opening. Light reflected (to the left side as shown in FIG. 5) by the mirror 59 having an opening illuminates the fundus of an eye 62 being examined, through an objective lens 61. As is conventionally known to one of ordinary skill in the art, a working distance between the ophthalmologic apparatus and the eye 62 being examined is adjusted using the objective lens 61 and the two ring slit relay lenses 56 and 58 so that the ring slit 55 is substantially in an optically conjugal position with the cornea of the eye 62 being examined.

Figure 8:
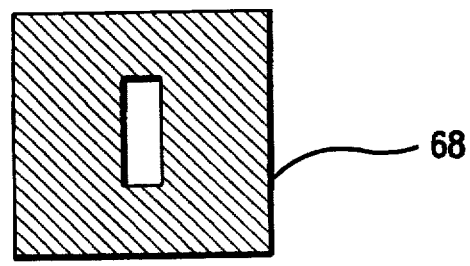
FIG. 8 is a view along the optical axis of an index mark plate included in the FIG. 5 embodiment showing a slit formed in the index mark plate.

The index mark projecting optical system includes an index mark projecting light source (point light source) 66 such as, for example, an infrared light emitting diode. Infrared light (indicated by the double-broken line in FIG. 5) emitted from the index mark projecting light source 66 illuminates an index mark plate 68 through an index mark projecting system relay lens 67a. A slit is formed in the index mark plate 68. As shown in FIG. 8, the long direction of the slit in the index mark plate 68 is parallel to a vertical axis of the paper.

Light that has passed through the slit in the index mark plate 68 is formed once into an image, which is incident on the dichroic prism 57 through an index mark projecting system relay lens 67b. The index mark projecting optical system light is reflected (upward as shown in FIG. 5) by the dichroic prism 57 and again is formed into an image near the mirror 59 by the ring slit relay lens 58. The index mark projecting light reflected (to the left as shown in FIG. 5) by the mirror 59 is then formed into an image near the pupil of the eye 62 being examined through the objective lens 61, and illuminates the fundus of eye 62.

In the illuminating optical system and the index mark projecting optical system, the dichroic prism 57 reflects infrared light while allowing visible light to pass through. Accordingly, the visible light from the observation-use light source 51 and the strobe tube 54 (photography-use illuminating light source) passes through the dichroic prism 57, but the infrared light from the observation-use light source 51 and the strobe tube 54 is reflected and leaves the illuminating optical system. Thus, the eye 62 fundus is illuminated by visible light from the observation-use light source 51 and the strobe tube 54 and infrared light from the index mark projection-use light source 66.

Accordingly, light from the index mark plate 68 slit is formed into an image near the dichroic prism 57 by the index mark projecting system relay lens 67b (indicated by the dotted line in FIG. 5) and is then reflected (upward as shown in FIG. 5). The reflected light is formed into an image at the rear side focal position of the objective lens 61 through the relay lens 58 and the mirror 59. Accordingly, light from the index mark projecting light source passing through the index mark plate 68 slit and the objective lens 61 is incident on the eye 62 being examined as substantially parallel light. As a result, if the eye 62 being examined is an eye with emmetropia, the index mark plate 68 slit is formed into an image on the eye 62 fundus. In other words, the slit image (character image) of the index mark plate 68 is defocussed in accordance with the diopter of the eye 62 being examined.

Figure 6:
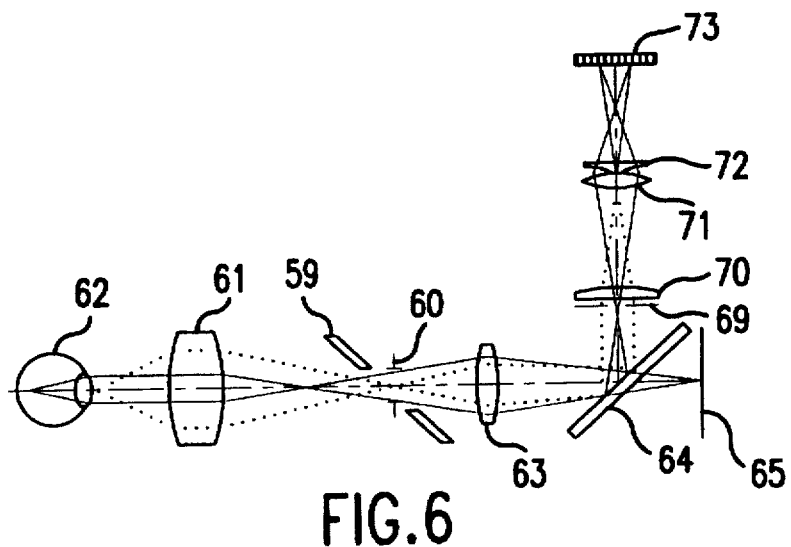
FIG. 6 is a schematic drawing showing a focus state detection system of the FIG. 5 embodiment.

The focus state detecting system extracted from the ophthalmologic apparatus is shown in FIG. 6. As indicated by the solid lines in FIG. 6, the slit image of the index mark plate 68, which has been projected onto the fundus of the eye 62 being examined, is formed into an image once by the objective lens 61, becoming a secondary light source. Next, the index mark plate 68 slit image passes through an open diaphragm 60 and the central opening of the mirror 59, and is incident on a focusing relay lens 63. Infrared light from the focusing relay lens 63 is incident on a dichroic mirror 64. The dichroic mirror 64 reflects infrared light and allows visible light to pass through. The light that is reflected (upward as shown in FIG. 6) by the dichroic mirror 64 is formed into an image once near a field diaphragm 69 and then impinges on a field lens 70. Light that has passed through the field lens 70 is incident on an array sensor 73 through a re-imaging lens 71 and a pupil dividing prism 72.

In contrast, the reflected visible light from the eye 62 fundus that was emitted by the observation-use light source 51 and the strobe tube 54 (photography-use illuminating light source) passes through the dichroic mirror 64 and is formed into an image on an imaging plane 65. A quick return mirror 78 is positioned between the dichroic mirror 64 and the imaging plane 65, as shown in FIG. 5. Accordingly, the reflected visible light from the eye 62 fundus that has passed through the dichroic mirror 64 is reflected (upward as shown in FIG. 6) by the quick return mirror 78 and is guided to an eyepiece lens 80 through a mirror 79 to be observed by an observer 90. The quick return mirror 78, the mirror 79, the eyepiece lens 80 and the observer 90 are shown in FIG. 5. In this manner, the eye 62 fundus being examined is observed through the eyepiece lens 80 and can be photographed at the imaging plane 65.

Because the dichroic mirror 64 reflects infrared light while allowing visible light to pass through, only the light from the index mark projection-use light source 66 that has passed through the index mark plate 68 reaches the array sensor 73. As a result, the index mark plate 68 image (slit image in the second preferred embodiment) formed on the array sensor 73 has good contrast.

The field diaphragm 69 is placed at a position that is optically conjugate with the array sensor 73 through the re-imaging lens 71. Further, the array sensor 73 is conjugate with the image plane (not shown) of the eyepiece lens 80 and the imaging plane 65. In the described embodiment, an eyepiece lens is used in the observing optical system; however, a TV-use optical system for observing with a TV monitor or the like can also be used.

The slit image (character image) from the eye 62 fundus being examined is formed into an image near the array sensor 73 by the re-imaging lens 71. When this occurs, the light rays that pass through the pupil dividing prism 72 are divided in two. Each of the divided light rays are formed into images on mutually different cells (areas) in the array sensor 73, as shown in FIG. 6.

Figure 9:
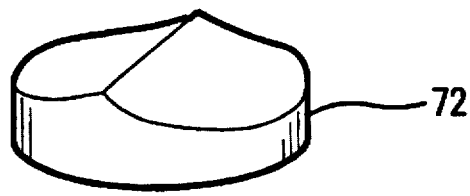
FIG. 9 is an oblique view of a pupil dividing prism of the FIG. 5 embodiment.

FIG. 9 shows an oblique view of the pupil dividing prism 72. For ease of illustration, in FIGS. 5 and 6, the ridge line of the pupil dividing prism 72 is drawn perpendicular to the plane of the paper. In actual use, the pupil dividing prism 72 would be rotated 90° about the optical axis so that the ridge line of the pupil dividing prism 72 is parallel with the plane of the paper. Further, in FIGS. 5-6, the direction of the arrangement of the cells in the array sensor 73 is also perpendicular to the plane of the paper to match the direction of the ridge line of the pupil dividing prism 22. However, in actual use, this axis also would be parallel with the plane of the paper. In other words, it is preferable that the long direction of the character plate 68 slit image and the direction of the ridge line of the pupil dividing prism 72 coincide.

Further, the ridge line of the pupil dividing prism 72 is substantially optically conjugate with the open diaphragm 60 through the focusing relay lens 63 and the field lens 70 (illustrated by the dotted lines in FIG. 6). The open diaphragm 60 corresponds to the exit pupil of the focus state detecting system, and consequently, the image on the array sensor 73 is an image formed by the light rays from the two different parts. The two images on the array sensor 73 obtained in this manner cause mutual sideways shifting in accordance with the front focus state and the rear focus state, as is conventionally known to one of ordinary skill in the art. Accordingly, the focus state can be detected by measuring the spacing (the distance) between the two images on the array sensor 73.

Figure 10:
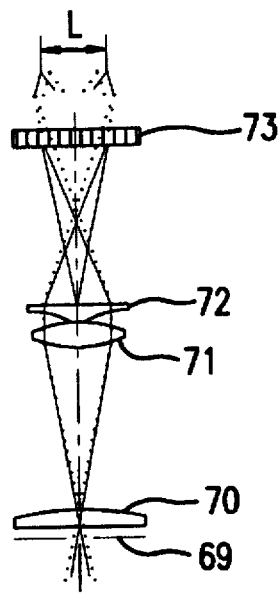
FIG. 10 is a schematic drawing showing the focus state detection system of the FIG. 5 embodiment.

The standard spacing (in-focus condition) between the two images on the array sensor 73 at the time of focussing is L, which is illustrated by the solid lines in FIG. 10. The image spacing is smaller than the standard spacing L when the ophthalmologic apparatus is in the rear focus state, which is illustrated by the dotted lines in FIG. 10, with the focal point to the rear (upward as shown in FIG. 10) of the field diaphragm 69. On the other hand, the spacing is greater than the standard spacing L when the ophthalmologic apparatus is in the front focus state (not shown in FIG. 10) with the focal point to the front (downward as shown in FIG. 10) of the field diaphragm 69.

In this way, the focus state information can be determined by measuring the spacing between the two slit images on the array sensor 73 and comparing the measured spacing with the in-focus standard spacing L.

Figure 11:
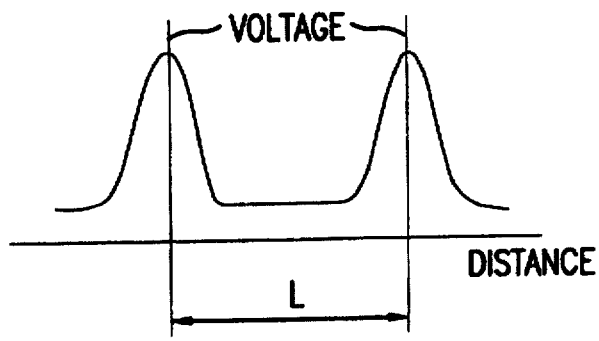
FIG. 11 shows the output waveform for focus state detection on a normal (i.e., non-cloudy) eye output by the FIG. 5 embodiment.
Figure 12:
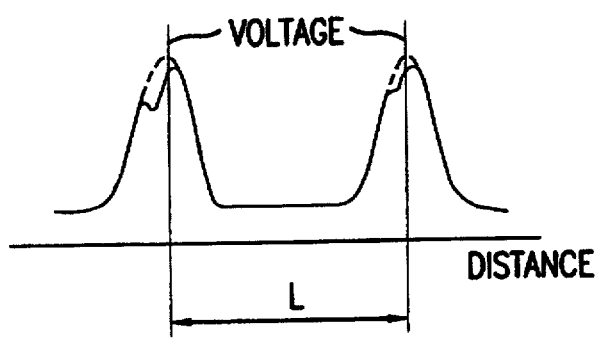
FIG. 12 shows the output waveform for focus state detection for an eye having partial crystalline lens cloudiness or partial vitreum cloudiness output by the FIG. 5 embodiment and also shows corrections made to that waveform by the present invention.

An example output waveform from the array sensor 73 when focus state detection is performed on a normal eye (i.e., without eyeball cloudiness) is shown in FIG. 11. An example output waveform from the array sensor 73 when the focus state detection is performed on an eye having partial crystalline lens cloudiness or partial vitreum cloudiness is shown in FIG. 12. Normal eye focus state detection does not create waveform disorder in the output waveform from the array sensor 73. Accordingly, the spacing L between the two slit images on the array sensor 73 can be accurately measured based on the output waveform, as shown in FIG. 11. Thus, focus state information can be accurately obtained through comparison with the standard spacing L when the ophthalmologic apparatus is in focus.

However, when there is partial crystalline lens cloudiness, partial vitreum cloudiness or other partial obstruction in the eyeball of the eye being examined, it is difficult to accurately measure the spacing between the two slit images on the array sensor 73 based on the output waveform. Naturally, when the eyeball of the eye 62 being examined is uniformly cloudy, the spacing between the slit images can be measured with some degree of accuracy by increasing the amount of light. However, partial cloudiness or the like in the eye 62 being examined creates waveform disorder in the output waveform of the array sensor 73, as shown in FIG. 12. As a result, it is very difficult to accurately detect the spacing L between the slit images, and therefore, the focus state information, using the output waveforms from the array sensor 73 under these conditions.

As shown in FIG. 5, each of the cells of the array sensor 73 is driven in succession based on a signal from a driving circuit 74, and the photoelectrically converted signal corresponding to each cell is output in succession from the array sensor 73 to a microcomputer 75. According to the present invention, in the microcomputer 75, the output waveform from the array sensor 73 can be stored in memory and then analyzed to determine whether there is a disorder such as a discontinuous part or an irregular part in the output waveform. As detailed above, standard techniques can be used to determine whether there are discontinuous or irregular parts of a waveform. Where a discontinuous part or an irregular part in the output waveform is determined, the discontinuous part or the irregular part is interpolated to correct the output waveform (indicated by the dashed line in FIG. 12). As detailed above, various well known techniques for eliminating discontinuities and irregularities in waveforms can be employed. In this way, the spacing L between the slit images, and hence the focus state information, is accurately detected from the corrected waveform. In other words, the waveform corrected by interpolating the disordered components or the like of the output waveform is used to determine the spacing between the slit images. In particular, the microcomputer 75 includes a waveform rectifying unit that is used to rectify the output waveform by correcting the waveform disorder caused by partial cloudiness or the like in the eye 62 being examined.

The rectified waveform is supplied to a computation unit 76. In the computation unit 76, the spacing between the two slit images is measured based on the rectified waveform and then compared with the in-focus standard spacing of the ophthalmologic apparatus. A motor M is driven by the motor driving device 77 based on the focus state information received from the computation unit 76. Thus, the focussing relay lens 63 is moved along the appropriate optical axis, and the eye 62 fundus being examined is focussed on the array sensor 73, the imaging plane 65 and the eyepiece lens 80 image plane (not shown).

In the second preferred embodiment, precise focus state detection is performed even when there is partial crystalline lens cloudiness or partial vitreum cloudiness in the eyeball of the eye 62 being examined. Further, to a certain probability, the degree of cloudiness in the eye 62 being examined is determined based on an amount of waveform disorder in the output waveform. The determined degree of cloudiness can then be converted into a numerical value, which is displayed on a TV monitor (not shown) or the like.

Two examples of eye examination devices have been described in which the output signal of a light receiving element (that receives light reflected from the eye fundus) is analyzed to determine whether the waveform of the output signal has any disorders, such as can be caused by partial cloudiness or other partial obstruction of the eye. When such disorders are detected, the output waveform is rectified so as to remove the disorders. The rectified waveform can then be used as usual in the eye examination apparatus.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention as defined in the following claims.

What is claimed is:

1. An eye examination apparatus, comprising:

a light projecting optical system including a light source that projects light onto a fundus of an eye being examined;

a light-receiving element that receives light reflected from the eye fundus and outputs a waveform signal representing a characteristic of the received reflected light;

a waveform rectifying device that rectifies the waveform signal output by the light-receiving element when the waveform signal includes disorders caused by a partial obstruction in the eye so as to eliminate the disorder and so as to output a rectified waveform signal; and an examining device that examines a condition of the eye based on the rectified waveform signal.

2. The apparatus according to claim 1, wherein the eye examination apparatus is an eye refractive power measuring apparatus, the output waveform signal represents a refractive power of the eye, and the examining device measures the refractive power of the eye based on the rectified waveform signal.

3. The apparatus according to claim 1, wherein the eye examination apparatus is an ophthalmologic apparatus, the output waveform signal represents a focus state of the ophthalmologic apparatus on the eye being examined, and the examining device is a focus state detector that determines a focus state of the ophthalmologic apparatus based on the rectified waveform signal.

4. The apparatus according to claim 1, wherein the partial obstruction is at least one of a partial crystalline lens cloudiness and a partial vitreum cloudiness in the eye.

5. The apparatus according to claim 4, wherein the examining device determines a degree of cloudiness in the eye based on the characteristic of waveform disorder in the waveform signal.

6. The apparatus according to claim 5, further comprising a display that displays a value representative of the degree of cloudiness.

7. The apparatus according to claim 1, wherein the light projecting optical system forms a predetermined image on the eye fundus in one of visible light and infrared light.

8. The apparatus according to claim 1, wherein the waveform rectifying device rectifies the output waveform signal by interpolating the output waveform signal.

9. The apparatus of claim 1, further comprising a photographing optical system that permits observing and photographing of the eye fundus illuminated by the light projecting optical system.

10. The apparatus of claim 1, further comprising means for analyzing the output waveforms to determine whether there are discontinuous parts or irregular parts in the output waveforms.

11. An eye examination apparatus, comprising:

light projecting means for projecting a light image onto a fundus of an eye being examined;

photo-conversion means for receiving light reflected from the eye fundus and outputting a waveform signal representing the received reflected light; and waveform rectifying means for determining whether the waveform signal output by the light-receiving means includes a waveform disorder caused by a partial obstruction in the eye and for eliminating the disorder when the disorder is determined so as to output a rectified waveform signal.

12. The apparatus according to claim 11, wherein the apparatus is an eye refractive power measuring apparatus, the output waveform signal represents a refractive power of the eye, and further comprising means for determining the refractive power of the eye based on the rectified waveform signal.

13. The apparatus according to claim 11, wherein the apparatus is an ophthalmologic apparatus, the output waveform signal represents a focus state of the ophthalmologic apparatus on the eye being examined, and further comprising means for determining a focus state of the ophthalmologic apparatus on the eye based on the rectified waveform signal.

14. The apparatus according to claim 11, wherein the partial obstruction is at least one of a partial crystalline lens cloudiness and a partial vitreum cloudiness in the eye.

15. The apparatus according to claim 14, wherein the waveform rectifying means determines a degree of cloudiness in the eye based on a characteristic of the waveform disorder in the output waveform signal.

16. The apparatus according to claim 15, further comprising display means for displaying a value representative of the degree of cloudiness.

17. The apparatus according to claim 11, further comprising means for analyzing the output waveforms to determine whether there are discontinuous parts or irregular parts in the output waveforms.

18. A method of examining an eye, comprising the steps of:
projecting light onto a fundus of an eye being examined;
receiving light reflected from the eye fundus with a light-receiving element that outputs a waveform signal representing the received reflected light;
determining whether a waveform disorder caused by a partial obstruction in the eye exists in the output waveform signal;
rectifying the detected waveform disorder in the output waveform signal by eliminating the disorder to output a rectified waveform signal; and
examining a condition of the eye based on the rectified waveform signal.

19. The method according to claim 18, wherein the examined condition is a refractive power of the eye, and the rectified waveform signal represents the refractive power of the eye.

20. The method according to claim 18, wherein the examined condition is a focus state of an ophthalmologic apparatus on the eye, and the rectified waveform signal represents the focus state.

21. The method according to claim 18, wherein the partial obstruction is at least one of a partial crystalline lens cloudiness and a partial vitreum cloudiness in the eye.

22. The method according to claim 21, further comprising the step of determining a degree of cloudiness in the eye based on a characteristic of the detected waveform disorder in the output waveform signal.

23. The method according to claim 22, further comprising the step of displaying a value representative of the degree of cloudiness on a display device.

24. The method according to claim 18, further comprising the step of analyzing the output waveforms to determine whether these are discontinuous parts or irregular parts in the output waveforms.

25. An eye refractive power measuring apparatus, comprising:
a light-receiving element that receives light reflected from a fundus of an eye being examined and outputs a waveform signal representing the refractive power of the eye;
a waveform rectifying device that rectifies the waveform signal output by the light-receiving element when the waveform signal includes a disorder caused by a partial obstruction in the eye being examined so as to eliminate the disorder and so as to output a rectified waveform signal; and
a measuring device that measures the refractive power of the eye based on the rectified waveform signal.

26. The eye refractive power measuring apparatus according to claim 25, wherein the measuring device determines a degree of cloudiness in the eye based on the characteristic of waveform disorder in the waveform signal.

27. The eye refractive power measuring apparatus according to claim 26, further comprising a display that displays a value representing the degree of cloudiness of the eye.

28. The eye refractive power measuring apparatus according to claim 25, further comprising means for analyzing the output waveforms to determine whether there are discontinuous parts or irregular parts in the output waveforms.

29. An ophthalmologic apparatus, comprising:
an index mark projecting optical system that projects a character onto the fundus of an eye being examined;
a light-receiving element that receives light reflected from the eye fundus and outputs a waveform signal representing a characteristic of received reflected light;
a waveform rectifying device that rectifies the waveform signal when the waveform signal includes a disorder caused by partial cloudiness in the eyeball, so as to eliminate the disorder and so as to output a rectified waveform signal; and
a focus state detecting system that determines a focus state of the ophthalmologic apparatus on the eye based on the rectified waveform signal.

30. The ophthalmologic apparatus of claim 29, wherein the focus state detecting system detects a degree of cloudiness in the eye based on a characteristic of the waveform disorder in the output waveform signal.

31. The ophthalmologic apparatus of claim 30, further comprising a display that displays a value representing the degree of cloudiness.

32. The ophthalmologic apparatus of claim 29, further comprising:
an illuminating optical system that emits illuminating light on the fundus of the eye; and
a photographing optical system that enables observing and photographing of the eye fundus illuminated by the illuminating optical system.

33. The ophthalmologic apparatus of clam 29, further comprising means for analyzing the output waveforms to determine whether there are discontinuous parts or irregular parts in the output waveforms.

* * * * *